United States Patent
Ruseler-van Embden et al.

(10) Patent No.: US 6,723,354 B1
(45) Date of Patent: Apr. 20, 2004

(54) METHODS AND MEANS FOR PREVENTING OR TREATING INFLAMMATION OR PRURITIS

(75) Inventors: Johanna Geertruida H. Ruseler-van Embden, Berkenwoude (NL); Leonarda Maria C. van Lieshout, Rotterdam (NL); Jon Daniël Laman, Amsterdam (NL)

(73) Assignee: Erasmus Universiteit Rotterdam, Rotterdam (NL)

(*) Notice: Subject to any disclaimer, the term of this patent is extended or adjusted under 35 U.S.C. 154(b) by 0 days.

(21) Appl. No.: 09/716,612

(22) Filed: Nov. 20, 2000

Related U.S. Application Data

(63) Continuation of application No. PCT/NL99/00312, filed on May 20, 1999.

(30) Foreign Application Priority Data

May 20, 1998 (EP) .............................................. 98201694

(51) Int. Cl.[7] ........................ A01K 65/00; A61K 35/78; A61K 49/00
(52) U.S. Cl. ......................... 424/725; 424/773; 424/91
(58) Field of Search ............................... 424/725, 773, 424/9.1

(56) References Cited

U.S. PATENT DOCUMENTS

| | | | | |
|---|---|---|---|---|
| 3,950,509 A | * | 4/1976 | Gerks et al. | .................. 424/65 |
| 4,906,457 A | * | 3/1990 | Ryan et al. | .................... 424/59 |
| 5,614,198 A | * | 3/1997 | Kennedy et al. | ......... 424/195.1 |

FOREIGN PATENT DOCUMENTS

| | | |
|---|---|---|
| EP | 0 564 307 A1 | 10/1993 |
| GB | 2 311 727 A | 10/1997 |
| JP | 06025000 | 1/1994 |
| WO | WO 95/12408 | 5/1995 |
| WO | WO 97/04792 | 2/1997 |

OTHER PUBLICATIONS

Pearce et al. Archives of Biochemistry and Biophysics. Feb. 1982. Vol 213, No. 2, pp. 456–462.*
Rodis et al. Plant Physiol. (1984). 74, 907–911.*
Radoev et al. Nauchni Tr., Vissh Inst. Khranitelna Vkusova Prom. Plovdiv (1964), 11, 265–270.*
Worowski et al. Acta Pol. Pharm. (1973), 30(4), 453–457.*
Frenkel et al., "Chymotrypsin–specific protease inhibitors decrease H2O2 formation by activated human polymorphonuclear leukocytes", Sep. 1987, pp. 1207–1212, Carcinogenesis, vol. 8, No. 9.
Keilova et al., "Naturally occurring inhibitors of intracellular proteinases", 1977, pp. 1873–1881, Acta Biol. Med. Germ, vol. 36.
Yahagi et al., "Manufacture of soybean extracts containing trypsin inhibitors for controlling skin disorders", Jul. 8, 1997, Abstract No. 127:126636.
Genell et al., "Protease Inhibitors in Plasma and Faecal Extracts from Patients with Active Inflammatory Bowel Disease", Jun. 1986, pp. 598–604, Scand. J. Gastroentenol.
Hutton et al., "Mucolysis of the colonic mucus barrier by faecal proteinases: inhibition by interacting polyacrylate", Mar. 1990. pp. 265–271, Clinical Science, vol. 78.

* cited by examiner

*Primary Examiner*—Sandra E. Saucier
*Assistant Examiner*—Vera Afremova
(74) *Attorney, Agent, or Firm*—TraskBritt

(57) ABSTRACT

The invention relates to methods and means for preventing, treating or reducing inflammation by inhibiting proteolytic activity. Specifically, the invention relates to preventing or reducing inflammations in the skin or intestine. The invention provides a method for reducing or preventing an inflammation by subjecting a mammal to treatment with at least one inhibitor which is capable of inhibiting proteolytic activity. In a preferred embodiment of the invention, the inhibitor is a plant product such as potato juice or a derivative thereof.

11 Claims, 7 Drawing Sheets

(2 of 7 Drawing Sheet(s) Filed in Color)

|      | Euro 1 | Euro 2 | Euro 3 |
|------|--------|--------|--------|
| 10%  | 35.7   | 27.4   | 7.5    |
| 5%   | 55.2   | 40.9   | 12.3   |
| 2%   | 83.5   | 67.7   | 26.3   |
| 1%   | 100.8  | 80.8   | 40.3   |
| 0.50%| 114.1  | 92.4   | 64     |
| 0%   | 131.2  | 129.9  | 144.7  |

|       | Euro 1 | Euro 2 | Euro 3 |
|-------|--------|--------|--------|
| 10%   | 73     | 79     | 95     |
| 5%    | 58     | 69     | 92     |
| 2%    | 36     | 48     | 82     |
| 1%    | 23     | 38     | 72     |
| 0.50% | 13     | 29     | 56     |

|       | Euro 1 | Euro 2 | Euro 3 |
|-------|--------|--------|--------|
| 10%   | 15.9   | 6      | 2.7    |
| 5%    | 22     | 12.9   | 4.5    |
| 2%    | 39     | 26.8   | 8.7    |
| 1%    | 49.9   | 42     | 14.2   |
| 0.50% | 87.7   | 63.8   | 22.6   |
| 0%    | 105.4  | 108.5  | 110.9  |

|       | Euro 1 | Euro 2 | Euro 3 |
|-------|--------|--------|--------|
| 10%   | 85     | 94     | 98     |
| 5%    | 79     | 88     | 96     |
| 2%    | 63     | 75     | 92     |
| 1%    | 53     | 61     | 87     |
| 0.50% | 17     | 41     | 80     |

|  | Euro 1 | Euro 2 | Euro 3 |
|---|---|---|---|
| 10% | 4.6 | 1.6 | 0 |
| 5% | 5.8 | 2.9 | 0 |
| 2% | 8.4 | 6.1 | 1.3 |
| 1% | 12.5 | 10.1 | 2.7 |
| 0.50% | 13.4 | 15.1 | 4.7 |
| 0% | 42 | 40.6 | 29.2 |

|  | Euro 1 | Euro 2 | Euro 3 |
|---|---|---|---|
| 10% | 89 | 96 | 100 |
| 5% | 86 | 93 | 100 |
| 2% | 80 | 85 | 96 |
| 1% | 70 | 75 | 91 |
| 0.50% | 68 | 63 | 84 |

|      | Euro 1 | Euro 2 | Euro 3 |
|------|--------|--------|--------|
| 10%  | 20.1   | 23.7   | 10.5   |
| 5%   | 32.3   | 42.7   | 14.5   |
| 2%   | 61.7   | 52.6   | 19.9   |
| 1%   | 104.6  | 83.3   | 25.2   |
| 0.50%| 135.6  | 122.9  | 34.3   |
| 0%   | 170.3  | 170.3  | 171.8  |

|      | Euro 1 | Euro 2 | Euro 3 |
|------|--------|--------|--------|
| 10%  | 88     | 86     | 94     |
| 5%   | 81     | 75     | 92     |
| 2%   | 64     | 69     | 88     |
| 1%   | 39     | 51     | 85     |
| 0.50%| 20     | 28     | 80     |

|  | Euro 1 | Euro 2 | Euro 3 |
|---:|---:|---:|---:|
| 10% | 10.2 | 0 | 3.1 |
| 5% | 13 | 10.5 | 5.2 |
| 2% | 19.4 | 18.6 | 7.2 |
| 1% | 27.5 | 27.2 | 10.7 |
| 0.50% | 53.1 | 43.2 | 12.8 |
| 0% | 123.1 | 135.1 | 123.1 |

|  | Euro 1 | Euro 2 | Euro 3 |
|---:|---:|---:|---:|
| 10% | 92 | 100 | 97 |
| 5% | 89 | 92 | 96 |
| 2% | 84 | 86 | 94 |
| 1% | 78 | 80 | 91 |
| 0.50% | 57 | 68 | 90 |

METHODS AND MEANS FOR PREVENTING OR TREATING INFLAMMATION OR PRURITIS

RELATED APPLICATIONS

This application is a continuation of co-pending International Application No. PCT/NL99/00312, filed May 20, 1999, designating the United States of America, which itself claims priority from EP 98201694.1, filed May 20, 1998.

TECHNICAL FIELD

The invention relates to methods and means for preventing, treating or reducing inflammation by inhibiting proteolytic activity, more specifically, for preventing or reducing inflammations of skin or intestine.

Inflammations of skin (dermatitis) or intestine (enteritis) are of various origin. Initially, allergic reactions, infections with pathogenic micro-organisms, excoriation by chemical or physical means, and other causes are instrumental in causing an inflammation. These causal events are immediately followed by the necessary reaction of the body, resulting in an interplay of actions and events aiming at restoration of the skin or intestine to its original state. In this interplay of cause and effect, various activities of proteolytic enzymes are seen. Granulocyte, mast cells, macrophages and other immediate actors in inflammatory responses and attracted by cytokines to a site of inflammation, contain and secrete proteases, such as chymotryptic protease and elastase, that act as mediators or are instrumental in cleaving and removing proteins derived from pathogens or from the surrounding degenerated tissue. Bacteria, either as primary causal agent or during a secondary infection, and other pathogenic micro-organisms, secrete proteases that damage the surrounding tissue for their purposes. In this battlefield between host and invader, excess proteolytic reactions are kept at bay by, often very specific, protease inhibitors. Well known are proteinase/proteinase inhibitor systems such as PMN-elastase/alpha-1-proteinase inhibitor and cathepsin G/alpha-1-antichymotrypsin.

Proteolytic enzymes in themselves, however, can also be a cause of inflammation. This is especially the case for digestive enzymes which are found in the intestinal tract. In order to degrade dietary protein, the stomach, the pancreas and the small intestinal brush border secrete several kinds of proteases. Pepsin from the stomach works optimal at pH 2, pancreatic and brush border enzymes, such as trypsin, chymotrypsin and elastase work optimal at pH 7–8. In adults, the small intestine has a length of seven meters and the transit time of its contents is about 3 hours. This part of the intestine is colonized by only a few bacteria but is filled with a watery mixture of food and a wide array and large quantities of digestive enzymes, such as lipases and proteases. However, in the large intestine, colon and caecum, the water content is greatly reduced and the activity of the enzymes is neutralized by bacteria. Neutralized and digested remnants of food and bacteria (feces) finally leave the body via the rectum. Only when the colon cannot effectively reduce the water content and neutralize the enzymes, the feces may still contain proteolytic activity, which, during periods of diarrhoea or fecal incontinence, may be very irritating to intra-anal and perineal skin.

The skin, especially of humans, is, although it is protected by the stratum corneum which consists mainly of keratine, as any other proteinaceous substance, very susceptible to the proteolytic action of proteases. Consequently, fluid-like small intestinal content may cause severe inflammation.

In babies and infants, the intestine is much less well developed, especially the colon, and functions different from that in adults. This is the reason why digestive enzymes in feces of babies and infants are not neutralized; the contents of feces resemble more the contents of the small intestine, albeit having passed the colon. Therefore, perineal (perianal) dermatitis is more often found with babies or infants than with adults. Also, hospitalized infants and children with gastro-intestinal disorders are prone to such a dermatitis. Such a dermatitis or prunitis, defined by itchiness, skin erythema, vesiculas, wetness, edema or disruption (excoriation) of perineal skin, is also found with diaper rash and can manifest itself in rather mild to very severe forms. With diaper rash, complicating factors are the accumulation of urine, whereby ureum is converted by fecal bacteria to ammonia, thereby raising the pH to an even better value for the activity of proteolytic enzymes. Since the skin is extremely susceptible to infections, care should be taken to prevent such inflammations related to fecal proteolytic activity.

Yet other cases of dermatitis are found with patients that have undergone resections of colon and/or ileum a-stoma. Pouchitis, an intestinal inflammation, is a major complication of ileoanal anastomosis with reservoir construction after colon resection and is characterized by clinical symptoms and inflammation of the reservoir (pouch). Peristomal (circumstomal) dermatitis is found with those patients that have been provided with an ileostoma that opens up at the surface of the abdomen, ending in an artificial reservoir that needs to be emptied daily. In inflammatory bowel diseases (IBD, such as Crohn's disease (CD), ulcerative colitis (UC) and pouchitis) and inflammation with an unknown etiology, the role of the intestinal flora and pathogens, proteolytic enzymes derived from these micro-organisms and endogenous (e.g., pancreatic or leukocyte/granulocyte) proteolytic enzymes and their contribution to degradation of protecting mucoglycoproteins and the underlying tissues, is not understood.

Especially in the above cases where the colon is removed or its function is affected or immature, it is evident that the proteolytic activity is still very high when the feces are excreted, leading to various degrees of perineal dermatitis.

It goes without saying that many medications and personal care items have been developed in order to remedy the severely itchy and often painful consequences of the above-discussed inflammations. General anti-inflammatory therapy often resorts to treatment with corticosteroids, despite the serious side-effects that are often seen with these medications. Other ways of treating are mainly based on providing either a protective layer to the skin, e.g., by applying a lipid-based ointment containing additives such as zinc, or by frequently cleaning an area at risk. Special personal care items have been developed, varying from specific wet wipes for perineal care, diapers that stay very dry despite heavy soiling by the child or patient, to products (stoma care appliances), such as adhesive, absorbing discs and stoma rinsing fluid that are specifically designed for stoma care patients with ileostomy or ileo-anal anastomosis.

However, none of these treatments can really do more than alleviate one or more of the above- and below-described clinical symptoms.

SUMMARY OF THE INVENTION

The invention provides a method for treating, reducing or preventing an inflammation or pruritis by subjecting a mammal to a treatment with at least one inhibitor which is capable of inhibiting proteolytic activity. Preferably, the invention provides a method whereby a protease produced or secreted, for example, granulocytes mastcells, macrophages and other actors in inflammatory processes, is inhibited. The invention is applicable to human and veterinary medicine and care.

A preferred embodiment of the invention is wherein the mammal is a human suffering from, for example, dermatitis or pruritis. Treating for example a dermatitis with a protease inhibitor reduces the proteolytic activity of the proteases involved in the inflammation pruritis. Especially when, in the interplay of causes and effects seen during inflammation, the activity of proteolytic enzymes is too high, the invention provides a method to reduce this activity (be it from host or from invader) by treatment with at least one inhibitor which is capable of inhibiting proteolytic activity.

The treatment is provided by applying the inhibitor in an ointment, cream, gel, powder, or any other suitable form to the location of the inflammation. These substances can, for example, also be carried on wipes impregnated with an inhibitor, in sprays or in rinsing fluid.

In a preferred embodiment of the invention, treatment is provided for an inflammation which is intestinal, perineal or peristomal, as is, for instance, seen with babies or infants with diaper rash, with children or adults with diarrhoea or fecal incontinence, with patients with inflammatory bowel syndrome and with stoma patients, which all suffer from the effects of proteolytic activity which is mainly fecal.

Treatment of fecal proteolytic activity can occur by applying the inhibitor in an ointment, cream, gel, powder, or any other suitable form, to the perineal or peristomal location of the inflammation. Intestinal inflammations, such as seen with IBD or pouchitis, can be treated by rinsing the affected location in the digestive tract by, for example, administering an enema, or can be administered orally, preferably in a pharmaceutical composition such as a draught or mixture pill, that can pass relatively unaffected through the esophagus and stomach.

These inhibitor substances can, for example, also be carried on wipes impregnated with an inhibitor, in sprays or in rinsing fluid. Also, it is possible to impregnate a diaper (during diaper production or shortly before use) with an inhibitor, thereby providing a method and means against diaper rash or pruritis. In a preferred embodiment, such a diaper is treated or impregnated with an inhibitor as provided by the invention in at least that diaper area (and underlying parts) that has, when in use, contact with the perineum of the baby, infant, child or adult. With diapers, the contact area normally comprises the diaper surface that is in contact with the perineum.

The invention provides a method of treatment which comprises administration to the patient or mammal prone to an inflammation of an inhibitor capable of inhibiting proteolytic activity of a protease. Inhibitors of proteolytic activity are widely known. For example, acid has an inhibiting effect on the hydrolysis of proteins by pancreatic proteases and, thus, a pH-decreasing substance can be used as an inhibitor as provided by the invention.

Also, adsorbing substances, such as activated charcoal (one such product is known as Norit), can act as a protease inhibitor through their adsorbing properties. In the experimental part, several examples are given of a treatment provided by the invention whereby activated charcoal, for example Norit®, is used to treat an inflammation such as, for example, pouchitis.

In a preferred embodiment of the invention, the invention provides methods and means capable of inhibiting proteolytic activity of a protease. Many protease inhibitors are known (see, for example, G. Salvesen and H. Nagase. Proteolytic enzymes, a practical approach. Eds R. J. Beynon and J. S. Bond In: The practical approach series. 1989). Although non-specific inhibitors are known (i.e., human plasma α-macroglobulin), most discriminate between protease classes or even subclasses. Substances such as peptide aldehydes or peptide chloromethyl ketones are very specific for subclasses of proteases (proteinases), depending on the peptide sequence they mimic. Others, such as metal chelators, act only against metallo-proteinases or calcium-dependent proteinases. Class-specific inhibitors are found against serine protease, cysteine protease, aspartic protease, and so on. These protease inhibitors are often commercially available as purified substances for use in biochemical preparations and may be expensive.

A preferred method according to the invention is a method wherein an inhibitor is derived from a plant, i.e., the inhibitor is a plant product comprising protease-inhibiting activity. As an example, such a product derived of a plant is activated charcoal which is obtained by burning peat or wood. A much preferred method according to the invention is a method wherein an inhibitor is derived from a plant that can give rise to fruit, seed, tubers or roots. "Derived" herein, for example, comprises derived by partial purification or isolation or by obtaining the necessary genetic information and producing by modern recombinant technology known in the art.

Plants often protect their leaves, fruits, seeds, tubers or roots against pests by inclusion of potent protease inhibitors and mixtures thereof in those leaves, fruits, seeds, tubers or roots. For example, cereals and legumes, such as wheat or soy beans, contain protease inhibitors such as soy bean trypsin inhibitor (SBTI), which generally has activity against trypsine or chymotrypsin but not against other proteinase classes. Tubers and roots, such as potato and cassave, and also yam, beets, sweetroot, and others, contain potent inhibitors of a wide variety of digestive tract proteases, such as aminopeptidases, carboxypeptidases, chymotrypsin, trypsin and elastase. Because of this broad range, tuber or root-derived plant products comprising proteolytic activity according to the invention are preferred. Potato tubers are an extraordinarily rich source of a variety of inhibitors of all major intestinal digestive endo- and exo-proteinase of animals (Pearce et al., Arch. Biochem. Biophys, 213, 456–462, 1982). Such inhibitors act as anti-nutrients that are present as part of the natural chemical defense mechanisms of plants, such as tubers and roots, against attacking pests. In potatoes, major inhibitors are polypeptide trypsin inhibitor (PTI), polypeptide chymotrypsine inhibitor I and II (PCI-I and PCI-II), inhibitor II against chymotrypsin and trypsine, and carboxypeptidase inhibitor, which all have analogues in other plants. These act alone and in concert against the major animal digestive proteinases.

The invention provides the use of an inhibitor or plant product or extract capable of inhibiting proteolytic activity for preparing a pharmaceutical or personal care composition for reducing or preventing an inflammation or pruritis. In the experimental part, an example is given of such a product which comprises, potato juice or an inhibitor derived thereof, for example, by freeze-drying. Such a composition can comprise an ointment, cream, gel, powder, or any other suitable form in which an inhibitor can be applied to a patient. In a preferred embodiment of the invention, provided is the use of an inhibitor or plant product capable of inhibiting proteolytic activity for preparing a composition for reducing or preventing an inflammation or pruritis which is an intestinal, perineal or peristomal inflammation or pruritis. Such a composition can be in the form of a rinsing fluid, can be contained in capsules that pass through the esophagus and stomach, or can be in prefabricated wipes or diapers where the inhibitor (or plant product) is added during production or shortly before use. In a preferred embodiment, the invention provides the use of an inhibitor capable of inhibiting proteolytic activity for preparing a personal or medical care composition for perineal, perianal and/or peristomal care, for example to counter proteolytic activity that is faecal.

For example, it is possible to prevent perineal dermatitis by rinsing the reservoir and the perineal skin with a protease inhibitor-containing fluid or a protecting ointment with protease inhibitors. Also, it is possible to pre-treat diapers or personal care compositions that adsorb soiling with inhibitor powder.

The invention provides the use of an inhibitor or plant product capable of inhibiting proteolytic activity for preparing a pharmaceutical or personal care composition wherein the inhibitor or product is derived from a plant, preferably wherein the plant can give rise to fruit, seed, tubers or roots, such as a potato plant. Such an inhibitor (product, composition or mixture), as explained above, is active against a protease which is selected from the group of pancreatic and granulocyte proteases. In a particular embodiment of the invention, the inhibitor (composition or mixture) is capable of inhibiting papain and/or pronase, illustrating its broad spectrum and effectivity.

The invention also provides a pharmaceutical or personal care product (for example, ointments, powder, fluids) comprising inhibitors of protease activity that is capable of:

(a) preventing inflammation or pruritis-caused by feces (fecal proteases by inhibiting proteolytic enzymes from pancreatic and brush border origin), from bacterial (gutflora) origin, from leucocyte (granulocyte, mastcell, macrophage) origin in the case of inflammation of the intestine; or (b) curing inflammation or pruritis caused by feces by, inhibiting proteases (such as elastase, cathepsins) produced by tissue (macrophages, granulocytes, mastcells); or (c) curing skin inflammation and other diseases in which inflammation and disease activity is related to infiltrating inflammatory cells (effectorcells) and the release of proteases; or (d) curing pruritis in general (treatment is often with antihistaminic) by local application of ointments with protease inhibitor which prevents histamine release from mastcells and protease release from fagocytes.

The invention also provides a personal care composition which can be added to rinsing fluids, wetties, powder, or ointments, for peri-anal and/or peri-stomal care or a diaper comprising an inhibitor of proteolytic activity. The invention furthermore provides a protease inhibitor for use in a method according to the invention. Attention to skin care can begin at the time of surgery, for example, inhibitor-containing rinse fluid. Inhibitors may be incorporated in stoma appliances, such as adhesive and absorbing discs and in stoma rinsing fluids and ointments.

Also, the invention provides a skin test for studying the effect of a protease inhibitor on proteolytic activity or inflammatory action of a substance, preferably of feces.

The invention is further described in the experimental part which is not meant to limit the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

In the drawings, which illustrate what is currently considered to be the best mode for carrying out the invention.

A. elastase, trypsin and α-chymotrypsin, end concentration of each of the enzymes 1% (Enzyme Mix) soluted in sterilized fecal supernatant from an ileostomy patient (FS)

B. FS

C. Euro 2 (end concentration 5%) soluted in FS with Enzyme Mix

D. Euro 2 in FS

After 24 hours, the test chambers were removed and the skin was rinsed with tap water. Sites were inspected for erythema and dermatitis after 1, 2, 4, 6 and 24 hours.

Figure 6:
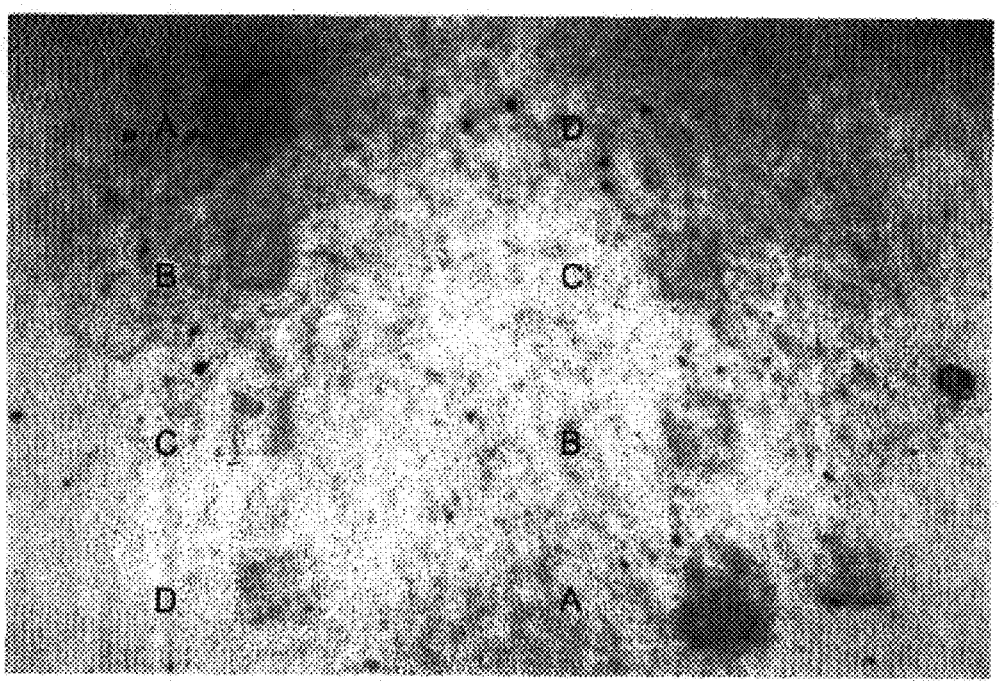
FIG. 6: Patch Test Chambers (van der Bend) of 10 by 10 mm, filled with 50 µl of a test solution were placed on the skin of the upper part of the back of 2 healthy subjects and fixed with Fixomull Stretch self adhesive tape; the distance between them was 15 mm. One series of 4 testchambers was placed from cranial to caudal, a second series from caudal to cranial. The test solutions had the following composition.
Figure 7A:
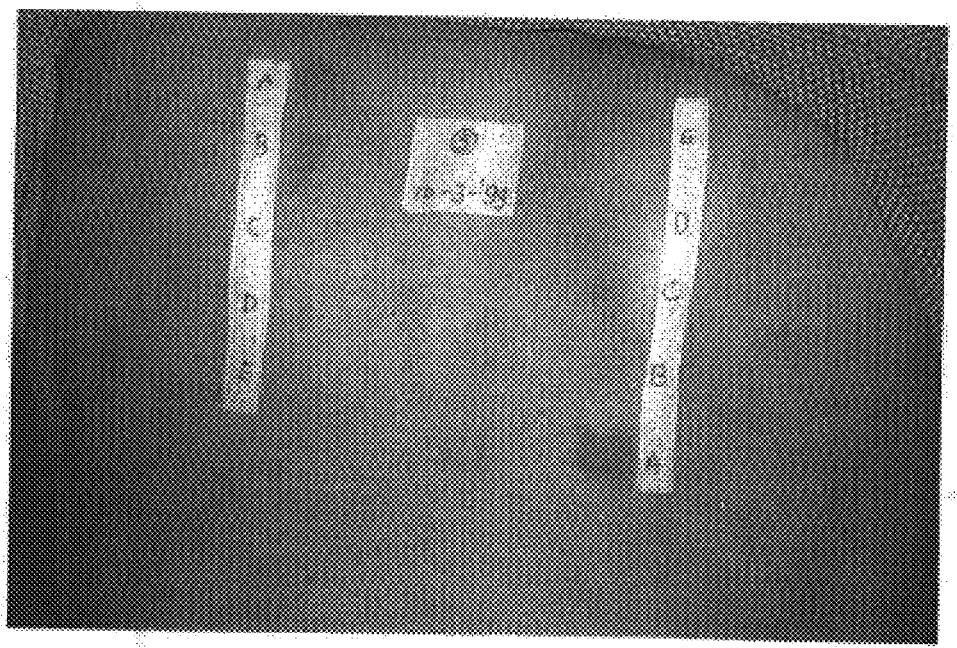
Figure 7B:
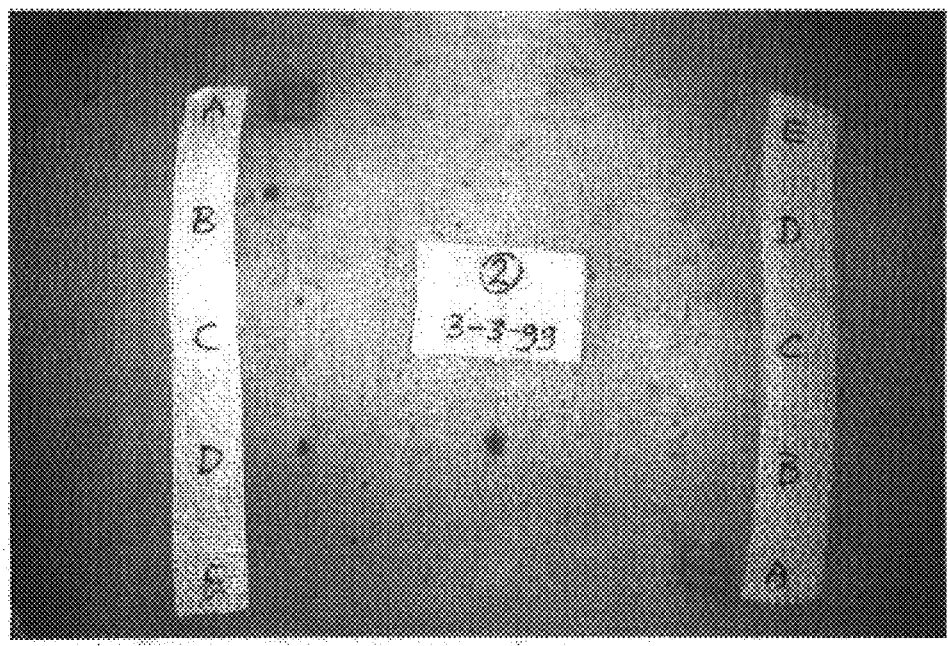

FIGS. 7A and 7B: The same patch test as described under FIG. 6, but the crude inhibitor fraction was replaced by the more purified fraction (EURO 3) .E.EURO 3 in distilled water.

Experimental Part

In adults, the small intestine has a length of seven meters and the transit time of its contents is about 3 hours. This is the reason why this part of the intestine is colonized by only a few bacteria, when compared to the large intestine. However the colon is colonized by large numbers of bacteria ($10^{10}$–$10^{11}$/gram). The transit is slow (24 hours) and the main function of the colon is absorption of water.

Finally, feces consist of one part solids and two parts of water. Half of the dry material are bacteria; the remnants are largely dietary fibre and host-derived material such as shed epithelial cells and mucus. The most active site of bacterial fermentation is the place where the contents of the ileum reaches the cecum. Abundant nutrients are available, the percentage of water is high and the flora has optimal conditions to multiply. Few data about this part of the (human) intestine are known, but the pH, measured in sudden death victims, is very low (pH 4.5–5.5).

The colon flora consist of 99.9% of obligate anaerobic bacteria; anaerobic-facultative aerobic bacteria such as coliforms are a minority (about $10^4$–$10^7$ bacteria/gram feces). The anaerobic colon flora is very stable and it is nearly impossible to induce alterations at species or genus level, even by drastic changes in diet (antibiotics or infection with enteropathogens, however, might disturb the resident flora). One of the causes of this phenomenon is that the most important nutrients are derived from endogenous material, digestive fluids, mucus, etc. A part of the digestive proteins (also the bile acids) are reabsorbed from the distal part of the ileum; the remainder is converted or digested in the colon. The colon flora is thought to play an important role in the inactivation of digestive pancreatic enzymes such as proteases.

In babies and infants, the intestine is much less well developed and the colon especially does not function as well as in adults. This is the reason why digestive enzymes in feces of babies and infants are not neutralized and/or reabsorbed. Its contents resemble more the contents of the small intestine, including a high proteolytic activity, albeit having passed the colon.

The principal endogenous nutrient sources are probably glycoproteins from gastric and intestinal mucus which contains up to 90% carbohydrate. Bacterial glycosidases degrade the oligosaccharide side chains which protect the glycoprotein from proteolytic destruction. When the protein core lacks the protection of the carbohydrates, it is no longer resistant to proteolysis by pancreatic and bacterial proteases. In the healthy colon, there is a balance between the production and the degradation of mucus.

Much attention has been paid to inflammatory bowel diseases (IBD): Crohn's disease (CD), ulcerative colitis (UC) and pouchitis. Pouchitis is a major complication of ileoanal anastomosis with reservoir construction and after colon resection for UC, and is characterized by clinical symptoms and inflammation of the reservoir (pouch). The role of the intestinal flora in IBD was investigated concerning pathogens and their contribution to degradation of the protecting mucus glycoproteins.

Patients with inflammations in the gut show a loss of the integrity of the mucosa. We have studied the potential harmful role of bacterial glycosidases and bacterial- and host-derived proteases by degrading mucus glycoproteins. Therefore, in patients with IBD, the composition of the intestinal flora and the activity of glycosidases and proteases was estimated. Also, enzymatic activity was measured in germ-free rats to establish the influence of the flora.

These studies showed that feces of patients with active CD, patients with an ileostomy and patients with a pouch, have a high proteolytic activity. Proteases enter the duodenum largely as secretions from the liver, brush-border and pancreas. A part of the activity is lost in the terminal ileum, probably due to absorbtion and/or action of endogenous inhibitors. In feces of healthy subjects, only a very low or no enzyme activity at all was estimated, which is probably largely of bacterial origin. However, germ-free animals, such as rats, show a high proteolytic activity throughout the whole large intestine. Patients with active IBD, ileostomy patients, and patients with a pouch, were found to have a high faecal proteolytic activity. From this, we may conclude that a complete colon flora and a normal (slow) transit is necessary to inactivate these enzymes.

The high proteolytic activity in feces of patients with IBD may cause an increased degradation of mucus glycoproteins and may play a role in the maintenance of the inflammation of the mucosa. In vitro experiments confirmed this hypothesis. The idea was born to treat patients such as those with an ileoanal anastomosis (IAA) with protease-inhibitors to prevent perineal dermatitis. Patients who are operated for UC or familial adenomatous polyposis (FAP), are considered for construction of an ileal reservoir after colon resection. This small reservoir is connected with the anus. The period after the operation is a hard time for most of the patients. Shortly after the operation, the patient's feces has a watery consistency, the patients are often not yet continent and this results in irritation and pruritis of the perineal skin (perineal dermatitis). The major cause of perineal dermatitis is the degradation of the epidermis (which consists largely of the protein keratin) by proteases.

Proteolytic activity was measured in feces of these patients and was found to be very high. Furthermore, 75% of the patients developed a moderate to severe perineal dermatitis; 25% did not have any sign of irritation.

Materials and Methods

Proteolytic Activity/subjects

Fecal samples from twenty-seven patients with Chron's disease (CD) were studied. Twelve patients, aged 27–58 years, had undergone intestinal surgery 3–12 years previously; locations of the resections were terminal ileum, ileum and cecum, and colon. A second group of patients was not operated; the principal sites of inflammation were ileum, ileum and colon, and colon. The diagnosis CD was established with the usual clinical, radiological and histopathological critria. All patients were outpatients.

Twelve healthy volunteers, aged 23–48 years were examined for comparison.

Ileostomy effluents were obtained from five adult patients with a conventional ileostomy (aged 38–71 years). They had undergone total colectomy more than five years before, for relief of CD or ulcerative colitis (UC), and were all currently in good health.

Fourteen patients with a pouch (median age 27 years) were studied. The patients had a restorative proctocolectomy for UC or familial adenomatous polyposis. An S pouch was constructed in 12 patients, whereas in two patients a W pouch was created. This study was performed at least one year after the restorative colectomy. The diagnosis pouchitis was based on clinical symptoms, endoscopic features of acute non-specific inflammation and histological evidence of an inflammatory cell infiltrate. Using these criteria, five patients presented pouchitis and nine did not (controls).

Fecal samples from thirteen patients operated for the construction of a reservoir with ileoanal anastomosis (IAA) were collected within 14 days after the operation. Proteolytic activity was measured in feces from 31 healthy children, aged 4 months to 7 years.

Proteolytic Activity/laboratory Animals

Feces from 4 conventional (Wistar) and 4 germ-free rats (Wag/Rij) were studied. From 2 conventional and 2 germ-free rats, the contents of the intestinal tract were studied.

Fecal samples from 20 colectomized dogs, purebred Beagles (Harlan), were collected. Three ileostomy groups were studied. In ten dogs a standard Brooke ileostomy was constructed by subtotal colectomy. In five dogs a valveless ileal reservoir (pouch) was fashioned by a side-to-side iso-antiperistaltic anastomosis. After a recovery period of 2 weeks, a schedule of increasing periods of occlusion was started, except for 5 dogs. The maximum tolerable occlusion time was 2.5–3 h for the ileostomy group and 4–7 h for the reservoir group. In five dogs a continent ileostomy (Kock's pouch) was constructed, which was emptied 2–5 times per 24 hours by catheterization.

Proteolytic Activity/faecal Samples and Intestinal Contents

Feces was frozen and stored at −20° C. within 3 h of passage. Preliminary studies showed no changes in proteolytic activity during at least 4 months of storage. Samples of 1 g were transferred to 24 vol of 0.1 M phosphate buffer pH 7.6 and homogenized ('Stomacher', Lab blender 400). Coarse particles were removed from the homogenates by gauze filtration (Utermohlen, refolded to 2 layers); these samples are further referred to as 'fecal homogenates'.

Immediately after killing the rats, the whole intestine was removed and prepared. The small intestine was divided into 4 parts of equal length and the contents of each part was carefully washed with 0.1 M phosphate buffer (pH 7.2). Samples from coecum and colon were treated in the same way as feces.

Proteolytic Activity/macrophages

Mouse peritoneal macrophages (RAW) were cultured in vitro in 200 ml DMEM with 5% FCS and 4 mM glutamine and stimulated with 200 U TNFαmol medium. After 18 hours, the cells were harvested, centrifuged and resuspended in 2 ml 0.1 M phosphate buffer pH 7.6. Total numbers of cells were about $3.10^8$ per ml. The cells were disrupted by repeated freezing and samples were used for protease assays.

Proteolytic Activity/enzyme Assay

Proteolytic activity was determined in the fecal homogenates in appropriate dilutions (up to 250-fold) in 0.1 M phosphate buffer (pH 7.6). Penicillin (0.1% w/v) was added to prevent bacterial growth. In the more recent inhibition tests, no penicillin was used. Samples of 0.1 ml were incubated with 0.1 ml 1% (w/v) azocasein (Sigma) in phosphate buffer at 37° C. during 1 h. The reaction was stopped by addition of 0.2 ml 10% (w/v) trichloroacetic acid (TCA). After 10 min at room temperature, unhydrolyzed azocasein, bacteria and other particles were removed by centrifugation at 10,000 rpm during 10 min. Then 0.1 ml of the clear supernatant was transferred to 0.1 ml of 1 N NaOH in flat bottom 24-wells microplates. To the blank assays, azoca-sein was added after incubation and addition of TCA. The absorption of the samples was measured at 450 nm and compared with standard curves obtained from solutions of azocasein. Proteolytic activity was expressed as milligrams; azocasein hydrolyzed during 1 h per gram dry or wet weight of sample. Each diluted sample was tested for other than enzymatic substrate hydrolysis after heating at 80° C. for 10 min. Spontaneous substrate hydrolysis was tested by incubation of the substrate with buffer.

N-succinyl-L-alanyl-L-alanyl-L-prolyl-L-leucine-p nitroanilide (Sigma) was used as substrate for estimating purified human leucocyte elastase (Sigma) and elastase activity from mouse macrophages. Samples of 0.1 ml were incubated with 0.1 ml substrate (0.1% w/v) in 0.1 M phosphate buffer pH 7.6 in a flat-well microtiter plate. After 30 or 60 min, the reaction was stopped by addition of 70 μl 30% acetic acid and the absorption was measured at 400 nm. One unit of enzyme was defined as the amount which released 1 μmol of p-nitoanilide per min at 37° C.

Proteolytic Activity/effect of pH

To test the effect of pH on the proteolytic activity, the fecal samples were diluted in citric acid-phosphate buffer (0.1 M $Na_2HPO_4/2H_2O$, 0.1 M citric acid/$H_2O$) pH 5.2, 5.8, 6.8 and 7.6. Additionally, the substrate solutions were made in appropriate buffers.

Preparation of Lectin-free Potato Proteins

Crude or relatively pure potato proteins were diluted in PBS. Human erythrocytes (disease-free) were added to potato proteins (end concentration of the ery's 3%), carefully mixed for 1 min, centrifuged for 2 min at 1500 rpm. The supernatant was mixed again with the erythrocytes. This was repeated 5 times untill no hemagglutination was found in a hemagglutination test. The reciprocal value of the highest dilution of potato protein that showed definite hemagglutination was defined as the hemagglutination titer. The hemagglutination titer decreased from 25.600 to 25-1, for example. After lyophilizing, the inhibitor activity of the lectins-free product was compared with the original protein fraction. No loss of inhibitor activity was found when tested in fecal samples with a high proteolytic activity and in purified protease solutions (trypsin, α-chymotrypsin and elastase, endconcentration 1%).

Furthermore, lectins-free potato proteins are obtained by using, for example, chitooligo-agarose (Seikagaku).

Lectins from potato proteins are also inactivated, not by removing them from the protein solution, but by binding to solube carbohydrate moieties, such as, for example, N-acetochitooligosaccharides from hydrolized chitin and glycoproteins from stomach or intestine. The lectins are still in the product but have lost their active site.

Proteolytic Activity/protease Inhibitors

The following inhibitors were used:

Trasylol (Aprotinin) (Bayer) not diluted

Ovomucoid () 1% (w/v), in 0.1 M phosphate buffer pH 7.6

Fetal Calf Serum (FCS) () not diluted

Trypsin inhibitor II-from Soybean (STI) (T-9003; Sigma) 1% (w/v) in phosphate buffer pH 7.6

Norit A (supra USP, 951191), B (Test EUR, A6910), E (Supra USP, 940260), PRSH, Carbomix, tablets Premium powder (Hollister)

Alternatively, potato juice (PJ) from "Bintjes" was prepared as follows. After peeling and washing, the potatoes were smashed to pieces, filtered through cambric under addition of 0.2% ascorbic acid. The juice was centrifuged at 27.500 RCF for 30 min at 4° C., filtered, through paper and again centrifuged. The clear yellow supernatant was filtered through a 0.45 micron filter and freeze-dried. This crude product was sterile (controlled with bloodagarplates) and contained about 25% protein. Ten gram PJ powder was derived of 200 ml juice.

Potato juice (PJ) from "Bintjes" was prepared as follows. After peeling and washing, the potatoes were smashed to pieces, filtered through cambric under addition of 0.2% ascorbic acid. The juice was centrifuged at 27.500 RCF for 30 min at 4° C., filtered through paper and again centrifuged. The clear yellow supernatant was filtered through a 0.45 micron filter and freeze-dried. This crude product was sterile (controlled with bloodagarplates) and contained about 25% protein. Ten gram PJ powder was derived of 200 ml juice.

In general, protease inhibitors which are present in potatoes, for example, can be recovered by grinding potatoes, removing starch and other solids, and, for example, freeze-drying the juice.

The purity of the protease inhibitor preparation can be improved by removing non-proteinaceous material and/or low molecular weight peptides and/or amino acids present in potato juice by, e.g., centrifugation, microfiltration, ultrafiltration, diafiltration or electrodialysis. Furthermore, protein can be selectively recovered in a relatively crude form from the potato juice matrix. This can be achieved by, e.g., ultrafiltration, iso-electric precipitation, (co) flocculation with polyelectrolytes or any other flocculation aid, co-precipitation with other proteins, protein precipitation with salt (salting out), or by changing the quality of the solvent, e.g., by adding acetone, methanol, ethanol or iso-propyl-alcohol, by iso-electric precipitation and thermal fractionation and other techniques known to anyone skilled in the art. Since protease inhibitors in potato juice are relatively heat stable, a moderate thermal treatment leads to denaturation and coagulation of less stable proteins. Coagulated protein can subsequently be removed by techniques as simple as, e.g., centrifugation. Although some protease-inhibiting activity is lost, the purity of the remaining protease inhibitors is increased. Even further purification is possible by ultrafiltration or by salting out the protease inhibitors, and subsequent removal of salt and other undesired components by ultra- and diafiltration. Alternatively, isolation of several protease inhibitors is possible by affinity chromatography, either directly from the crude potato juice matrix or after pre-purification.

In most of the experiments, the inhibitor was added to feces (diluted 1:25 in buffer), mixed for 5–15 min and added to the substrate; PJ-powder was added to undiluted feces (1:1) and after mixing, diluted (1:25) with buffer. In each experiment, controls were assayed (sterilized feces, sterilized inhibitors, buffer solutions).

Proteolytic Activity/purified Enzymes

The following enzymes were tested in the inhibition experiments:

bovine pancreatic trypsin (Serva)

bovine pancreatic α-chymotrypsin (Merck, Sigma)

bovine pancreatic elastase (Sigma)

papain (Sigma)

pronase (Sigma)

(carboxypeptidase and leucinaminopeptidase were tested, but did not hydrolyze azocasein)

All enzymes were used in a concentration of 0.2% (w/v) in buffer.

Proteolytic Activity/skin Tests

Skin tests were performed on the ventral part of the forearm. The following solutions were tested: 1. supernatant from feces of a patient with an ileum reservoir with a high proteolytic activity; 2. the same supernatant, but sterilized; 3. supernatant with 0.25% STI (w/v) and 4. 0.25% STI in buffer. Two hundred $\mu$l of each solution were placed on folded cambric on the skin and covered with plastic and adhesion wound pad. Total incubation time was 7 h, but after 3 and 5 h 100 $\mu$l buffer was added to each of the test patches to prevent dehydration.

Inhibition of Fecal Proteolytic Activity by Products from Potato Juice Euro 1, Euro 2, Euro 3

Euro 1 is crude PJ powder, Euro 2 and 3 are more purified.

Materials and Methods

Fecal Samples

Feces from 1 patient with an ileostomy, 1 patient with a good-functioning pouch, 1 patient 14 days after colectomy and the construction of a pouch, 2 babies aged 4 months were used.

Feces were used undiluted except for the babies, which was diluted 1:1 in phosphate buffer pH 7.6 and centrifuged 10 min at 10,000 g.

EURO's

EURO's were used as 1:5, 1:10, 1:25, 1:50 and 1:100 dilutions in phosphate buffer pH 7.6.

Feces and EURO were mixed 1:1 for 10 minutes, then the mixture was diluted in phosphate buffer pH 7.6 1:12.5.

In both dilutions, proteolytic activity was measured with azocaseine as substrate.

Skin tests

Patch Test Chambers (van der Bend) of 10 by 10 mm, filed with 50 $\mu$l of a test solution were placed on the skin of the upper part of the back of 2 healthy subjects and fixed with Fixomull Stretch self-adhesive tape; the distance between them was 15 mm. One series of 4 test chambers was placed from cranial to caudal, a second series from caudal to cranial.

The test solutions had the following composition:

A. elastase, trypsin and α-chymotrypsin, end concentration of each of the enzymes 1% (Enzyme Mix) soluted in sterilized fecal supernatant from an ileostomy patient (FS)

B. FS

C. Euro 2 (end concentration 5%) soluted in FS with Enzyme Mix

D. Euro 2 in FS

After 24 hours, the test chambers were removed and the skin was rinsed with tap water. Sites were inspected for erythema and dermatitis after 1, 2, 4, 6 and 24 hours.

A comparable skin test was made with the more purified potato protein fraction (EURO 3), end concentration 1%. A fifth test chamber was placed to control contact dermatitis: E (potato protein in distilled water). Twelve healthy subjects were tested.

Allergy Tests

Type 4 (contact dermatitis): 31 patients of the department of Dermatology (AZR) were tested with the relatively purified (Euro 3) potato protein according to standard protocols. Type 1 (IgE mediated): pricktests: 10 patients of the department of Allergy (AZR) with food allergy were tested and 1 patient with a severe allergy towards potato protein.

Results

1 Proteolytic Activity in Faeces

Proteolytic activity in feces from healthy subjects was low. However, Table 1 shows that patients with CD, ileostomy patients and patients with a pouch (with and without pouchitis) have a high proteolytic activity.

TABLE 1

Proteolytic activity in faeces of healthy subjects and patients

| | Proteolytic activity | | Dry weight of faeces mg/g | |
|---|---|---|---|---|
| | median | (range) | median | (range) |
| Healthy subjects | 17.9* | (7.5–44.0) | 313 | (164–403) |
| Patients with CD | | | | |
| no resections | 47.9 | (19.1–192.0) | 216 | (128–228) |
| resections | 228.7 | (130.6–356.6) | 134 | (84–175) |
| Patients with ileostomy | 336 | (89–972) | 88 | (69–120) |
| Patients with a pouch | | | | |
| no pouchitis | 14** | (5.5–23.5) | 83 | (57–103) |
| pouchitis | 14 | (7.1–17.3) | 52 | 30–110) |

TABLE 1-continued

Proteolytic activity in faeces of healthy subjects and patients

| | Proteolytic activity | | Dry weight of faeces mg/g | |
|---|---|---|---|---|
| | median | (range) | median | (range) |
| Patients with IAA | 53 | (18–105) | ND | (<30) |

*azocasein hydrolyzed, mg/h/g dry faeces
**azocasein hydrolyzed, mg/h/g wet faeces Comparable results were found in fecal samples of laboratory animals. Feces from normal dogs and rats had a very low proteolytic activity. Proteolytic activity was found to be high in ileostomy output and in valveless pouches of dogs despite occlusion; however, continent pouches showed a complete normalization concerning the proteolytic activity (and several other parameters which are not discussed in this context). In contrast with germ-free rats in the colon of conventional animals, the proteolytic activity is strongly decreased, which suggests a role for the colon flora in inactivation (and/or degradation) of digestive proteases. In infants, proteolytic activity varies with age. An estimate of the proteolytic activity in feces of healthy infants and children show in infants (n=10, 4–12 months) very high activity, in children (n=9, 1–2 years) lower, but still high activity and in children (n=12, 2–8 years) decreasing activity.

In a further experiment, the proteolytic activity in feces of 31 children was again found to decrease with age, in children of 4 months (n=4): 191 mg hydrolyzed azocasein/h/g feces, in children of 6 months (n=2): 109 mg, in a child of 8 months (n=1): 118 mg, in children of 11 months (n=3): 105 mg, in children of 16 months (n=3): 73 mg, in children of 24 months (n=6): 34 mg, in children of 3 years (n=5): 24 mg, in children of 5 years (n=3): 3 mg, in children of 7 years (n=4): 14 mg was found.

2 Inhibition of Proteolytic Activity pH

Figure 1A:
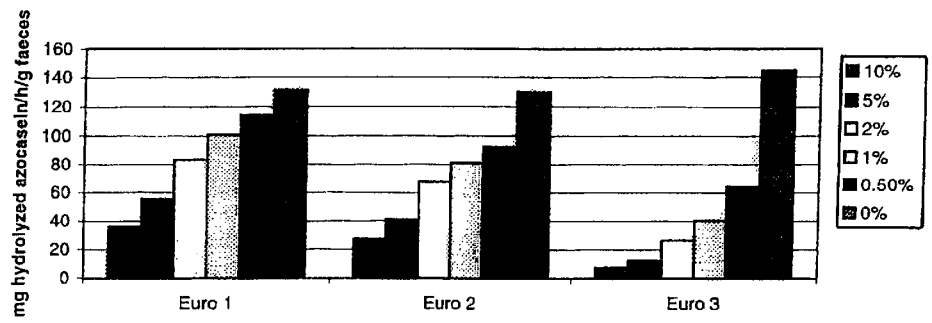
FIGS. 1A and 1B: Inhibition of fecal proteolytic activity by products from potato juice. Feces from 1 patient with a well-functioning pouch were used. Feces were used undiluted. EURO's were used as 1:5, 1:10, 1:25, 1:50 and 1:100 dilutions in phosphate buffer pH 7.6. Feces and EURO were mixed 1:1 for 10 minutes, then the mixture was diluted in phosphate buffer pH 7.6 1:12.5. In both dilutions, proteolytic activity was measured with azocaseine as a substrate.
Figure 1B:
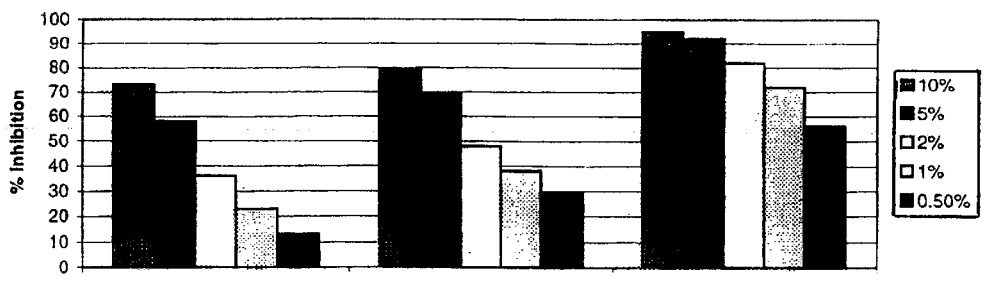
Figure 2A:
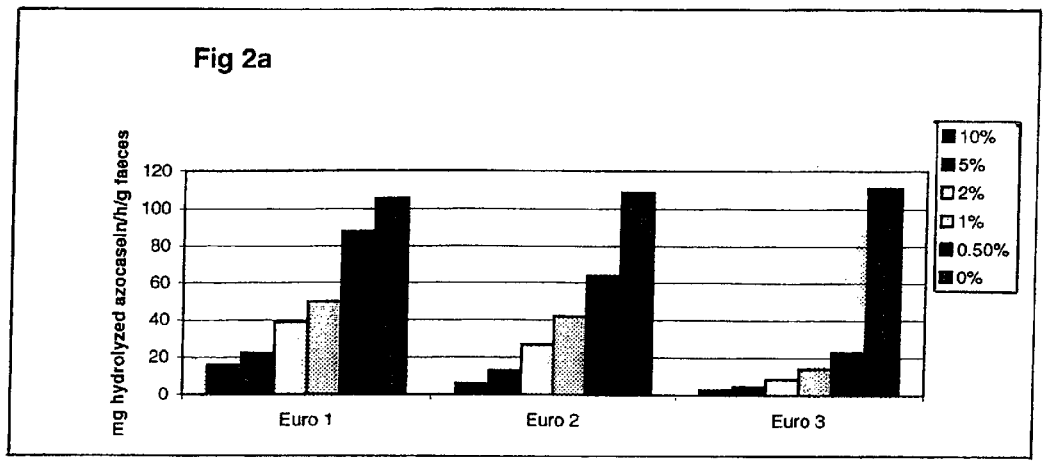
FIGS. 2A and 2B: Inhibition of fecal proteolytic activity by products from potato juice. Feces from 1 patient with an ileostomy were used. Feces were used undiluted. EURO's were used as 1:5, 1:10, 1:25, 1:50 and 1:100 dilutions in phosphate buffer pH 7.6. Feces and EURO were mixed 1:1 for 10 minutes, then the mixture was diluted in phosphate buffer pH 7.6 1:12.5. In both dilutions, activity was measured with azocaseine as a substrate.
Figure 2B:
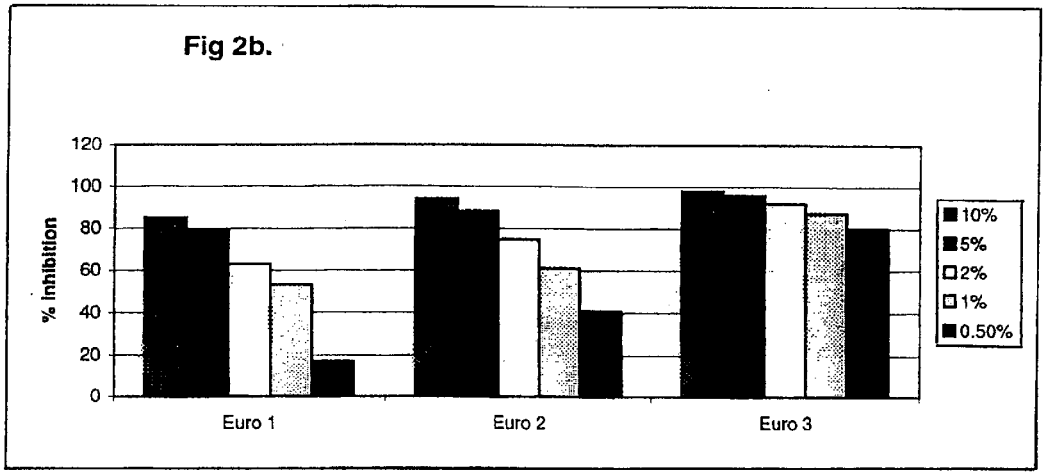
Figure 3A:
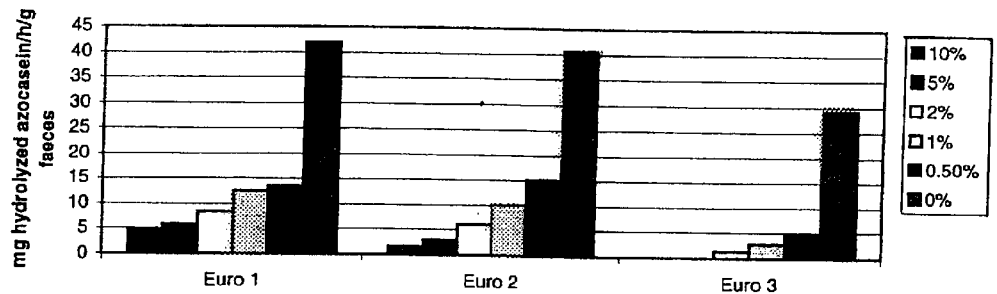
FIGS. 3A and 3B: Inhibition of fecal proteolytic activity by products from potato juice. Feces from 1 patient 14 days after colectomy were used. Feces were used undiluted. EURO's were used as 1:5, 1:10, 1:25, 1:50 and 1:100 dilutions in phosphate buffer pH 7.6. Feces and EURO were mixed 1:1 for 10 minutes, then the mixture was diluted in phosphate buffer pH 7.6 1:12.5. In both dilutions, proteolytic activity was measured with azocaseine as a substrate.
Figure 3B:
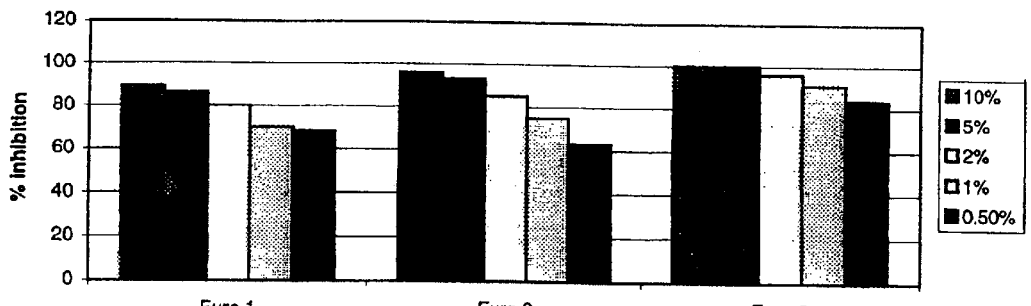
Figure 4A:
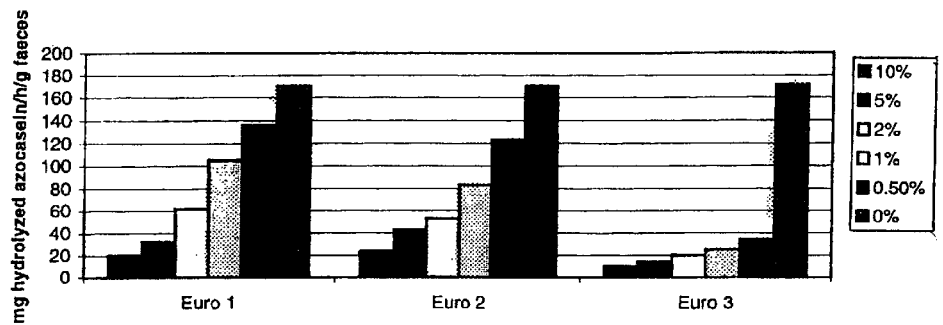
FIGS. 4A, 4B, 5A and 5B: Inhibition of fecal proteolytic activity by products from potato juice. Feces from 2 babies aged 4 months were used. Feces were used diluted 1:1 in phosphate buffer pH 7.6 and centrifuged 10 minutes at 10,000 g. EURO's were used as 1:5, 1:10, 1:25, 1:50 and 1:100 dilutions in phosphate buffer pH 7.6. Feces and EURO were mixed 1:1 for 10 minutes, then the mixture was diluted in phosphate buffer pH 7.6 1:12.5. In both dilutions, proteolytic activity was measured with azocaseine as a substrate.
Figure 4B:
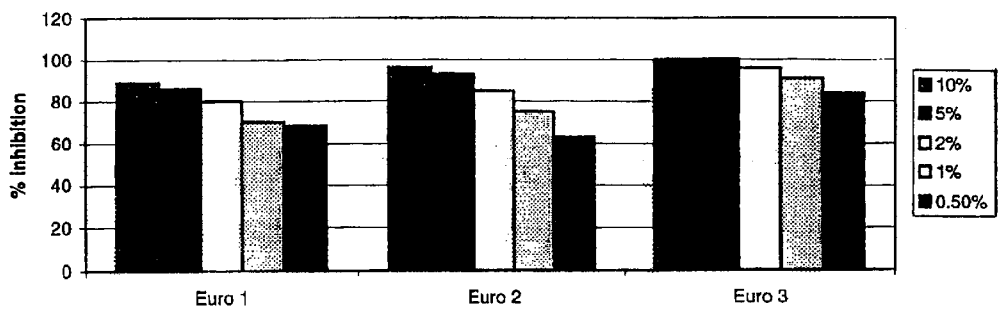
Figure 5A:
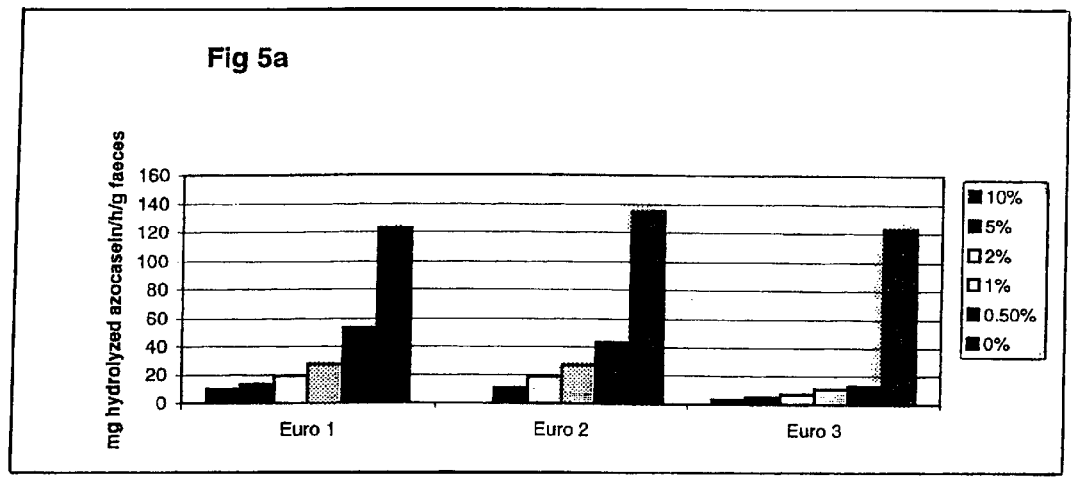
Figure 5B:
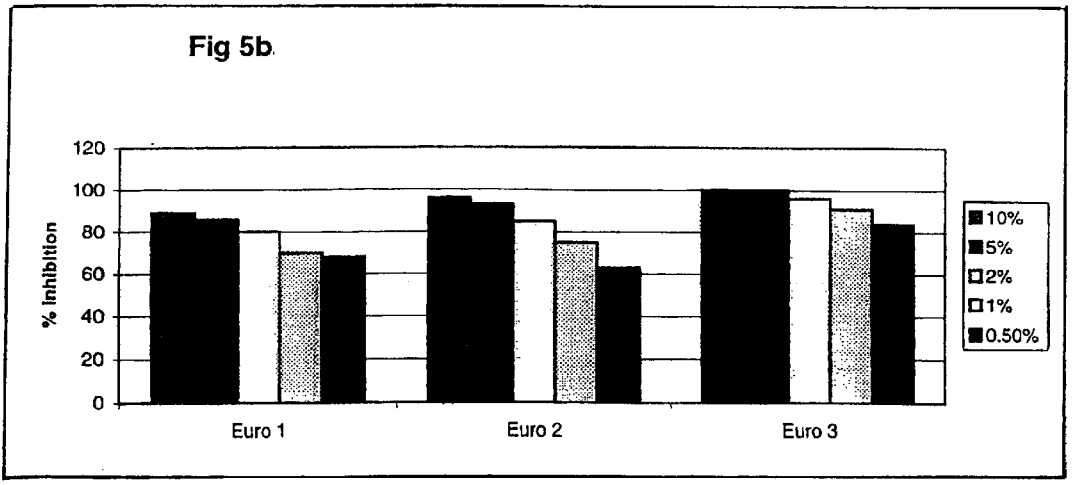

FIG. 3 shows that the pH dependence of the proteolytic activity was similar in each of the tested samples. At pH 6.8 and 7.6, the activities were, respectively, three and four times higher than at pH 5.2 (p<0.001 for both comparisons). This means that at pH of 5.2 the proteolytic activity is inhibited for 75%.

STI

The next table (Table 2) shows the results of our first experiments with protease inhibitors. Conditions of the assays were different but Trasylol, ovomucoid and FCS had effects on the proteolytic activity which were less promising or conflicting than STI. In a concentration of 1% (w/v), the inhibition was more than 80%.

TABLE 2

Inhibition of proteolytic activity in patients and dogs

| | % inhibition of the proteolytic activity | | | | | |
|---|---|---|---|---|---|---|
| | CD patients* | | Ileostomy dog | | pouch dog | |
| | n = 4 | n = 1* | n = 3° | n = 1† | n = 2⁺ | n = 1** |
| ovomucoid | 68 | 93 | 84 | 52 | | |
| trasylol | | | 54 | 56 | | 16 |

TABLE 2-continued

Inhibition of proteolytic activity in patients and dogs

| | % inhibition of the proteolytic activity | | | | | |
|---|---|---|---|---|---|---|
| | CD patients* | | Ileostomy dog | | pouch dog | |
| | n = 4 | n = 1* | n = 3° | n = 1† | n = 2⁺ | n = 1** |
| STI 1% (0.25,0.5,0.75%) | 93 | | 84 (63,61, 45) | | | |
| FCS | 94 | | 0 | | | |
| ovomucoid + trasylol | | | 51 | | | |
| ovo + tras + STI | | | | | 76 | |
| ovo + STI | | | 70 | | | |
| norit A | | | | | 50 | |

*inhibitor added to faeces 1:2000 diluted; 20 h incubated with substrate
°inhibitor added to faeces diluted 1:100; 2 h incubated
†undiluted faeces+ inhibitor (3 + 1), mixing for 2 h, then diluted 1:100
⁺undiluted faeces +norit (4 + 1) mixing for 2 h (or 13 min), then diluted 1:100
**2 g faeces+ 0.5 ml trasylol; mixing for 15 min, then diluted Norit Several kinds of norit were tested with feces from pouch patients with a high proteolytic activity for optimal adsorbing qualities, to be used as protease inhibitor in fluid to rinse IAA patients after their operation. In this experiment, Premium powder was tested also. Table 3 shows that the adsorbing capacities of norit PRSH and norit E for proteases were extremely strong.

TABLE 3

Effect of norit on proteolytic activity in faeces

| | % inhibition of the proteolytic activity* |
|---|---|
| Carbomix | 0 |
| Norit A (Serva) | 83 |
| Norit A | 63 |
| Norit B | 0 |
| Norit E | 97 |
| norit PRSH | 100 |
| norit tablets | 58 |
| premium powder | 17 |

Inhibition of the proteolytic activity by norit was confirmed by using skimmed milk plates; the caseine in the agar is hydrolyzed by proteases and clarification is seen after treatment with TCA.

Norit PRSH was tested in different concentrations at pH 5.2 and 7.6.

TABLE 4

Effect of Norit PRSH on proteolytic activity in faeces

| | % Inhibition of the proteolytic activity | |
|---|---|---|
| | pH 5.2 | ph 7.6 |
| Norit PRSH 1% | 76 | 36 |
| 2% | 95 | 92 |
| 3–5% | 100 | 100 |

Potato Juice (PJ)

PJ was initially prepared and tested as fluid; later on, a freeze-dried product was prepared. The initial end concen tration of the PJ powder in the fecal suspensions was 17%. Table 5 shows the inhibition of fecal proteolytic activity by PJ and PJ powder.

TABLE 5

Effect of PJ on proteolytic activity of faeces

| | % Inhibition of the proteolytic activity | | | |
|---|---|---|---|---|
| Number of patients | 4* | 4° | 7† | 7⁺ |
| PJ | | | | |
| undiluted | 93 | (50) | | |
| 1:5 diluted | 90 | | | |
| 1:10 diluted | 51 | | | |
| 1:25 diluted | 23 | | | |
| PJ powder | | | | |
| 17% (w/v) | | | 88 | 97 |
| 10% | | | 78 | 90 |
| 5% | | | 53 | 74 |
| 2% | | | 20 | 44 |

*faeces 1:12.5 diluted in buffer, then mixed with Pj (1 + 1)
°faeces and PJ 1:1 mixed for 15 min, centrifuged, 1:25 diluted
†faeces and PJ powder (1 g in 2 ml buffer) 1:1; this gives an end concentration of 17%; no further dilutions for the assay
⁺same experiment as † but the mixture was diluted 1:25 for the assay Heating of the PJ powder in a solution of 1 g in 4 ml buffer (end concentration in feces 5%) did decrease the inhibitor capacities as follows:

| unheated PJ: | 65% inhibition of the proteolytic activity |
|---|---|
| 30 min at 55° C.: | 64% |
| 30 min at 80° C.: | 47% |
| 30 min at 90° C.: | 24% |
| 30 min at 100° C.: | 14% |

Effect of protease inhibitors on the activity of pure enzymes is shown in Table 6. PJ powder is a very potent inhibitor of several pancreatic enzymes, papain and pronase.

TABLE 6

Effect of protease inhibitors on purified enzymes
% Inhibition of the proteolytic activity

| | trypsin | chymotrypsin | elastase | pronase | papain |
|---|---|---|---|---|---|
| STI (0.125%) | 99 | 99 | 15 | | |
| STI-A | 100 | 80 | 50 | 0 | 0 |
| STI-B | 100 | 100 | 60 | 0 | 0 |
| STI-C | 100 | 100 | 55 | 0 | 0 |
| Trasylol (undil.) | 95 | 95 | 10 | | |
| PJ* | 100 | 100 | 100 | 38 | 83 |
| PJ (30 min at 80° C. | | | | | |
| 1:5 | | | 100 | | |
| 1:10 | 100 | 100 | 97 | | |
| 1:30 | | | 95 | | |
| 1:40 | | | 94 | | |
| 1:50 | | | 91 | | |
| 1:75 | | | 90 | | |
| 1:100 | | | 88 | | |
| 1:1000 | | | 54 | | |

*1 g PJ powder was mixed with 2 ml and with 4 ml buffer

Testing of Trypsin Inhibitors from Soybeans

STI-A: STI-type I-S Sigma T 9003
STI-B: STI-type II-S Sigman T 9128
STI-C: Bowman-Birke Inhibitor Sigma T 9777 enzyme concentration was 0.02%, inhibitor concentration (end concentration) was 0.125%.

Possible interactions of the PJ-inhibitor with the substrate was tested by using different concentrations of azocasein in the same experiment. No interactions were found:

TABLE 7

| | % Inhibition of elastase (0.02%)-activity | |
|---|---|---|
| | 1% azocasein | 2% azocasein |
| PJ diluted: | | |
| 1:50 | 100 | 100 |
| 1:100 | 97 | 95 |
| 1:500 | 87 | 75 |
| 1:1000 | 65 | 66 |
| 1:2000 | 44 | 51 |

Skin Tests

After removing the pads and the cambric, the skin was carefully cleaned with tap water and judged immediately and after 1–18 h. No reaction was seen with sterilized feces (2) nor with STI in buffer (4); however, moderate redness, papulas and some vesiculas could be observed at location 1 (fecal supernatant). Location 3 (fecal supernatant with STI) showed a slight redness that disappeared within 60 min.

The effect of potato juice or inhibitors derived therefrom was also tested in vitro and in a skin test. The results are shown in FIGS. 1–6. It is possible to inactivate 90–100% of total proteolytic activity. Extracts from potato, such as potato juice, or inhibitors derived therefrom are able to inactivate fecal proteases and this prevents inflammation.

In the skin test, PJ, and its various purified fractions, were shown to be very effective when applied to treat and prevent an inflammation. Whereas, as sterilized fecal supernatant from an ileostomy patient caused an inflammation of the skin and a severe dermatitis (redness, edema, vesiculas, pain) when proteolytic enzymes were added, no inflammation was found when potato juice inhibitor was added in both cases. For example, ointments, such as creme or gels, when mixed with PJ inhibitor, are capable to inhibit or prevent the local dermatitis.

Furthermore, no allergic or other adverse reactions were observed against both the potato juice product.

Inhibition of Macrophage Proteases

The production of proteolytic enzymes by mouse macrophages was stimulated by TNFα. Addition of purified potato proteins (EURO 3) inhibited the activity of elastase-like proteases for 70%.

Elastase activity in mU
Macrophages ($6.10^8$ cells) 26.5
Macrophages ($6.10^8$ cells) +EURO 3 (1%) 8.0

These results show that the activity of (puried) human leucocyte elastase is reduced by potato protease inhibitors.

Discussion

Furthermore, these experiments show that patients with intestinal inflammations and/or resections of the colon or ileum, and also infants and children up to 2 years of age, have a high fecal proteolytic activity. These enzymes are of pancreatic, brush-border, microbial and/or cellular (granulocytes, macrophages) origin. These enzymes impair the protective intestinal mucus layer, as well as the skin, in the perineal zone.

Both crude and purified potato proteins (protease inhibitors) inhibit the activity of fecal proteases (hydrolyzing azocsein) and the activity of macrophage elastase (hydrolyzing N-succinyl-L-alanyl-L-alanyl-L-prolyl-L-leucin-p nitroanilide). Purified pancreatic enzymes, trypsin, chymotrypsin and elastase, are also inhibited by PJ(crude or purified).

In a skin test, dermatitis developed within 24 h of using purified pancreatic proteases dissolved in sterilized fecal supernatants. This test is microbiologically safe, but the additional effects of fecal compounds, such as bile acids, are intact. Dermatitis was completely prevented by the addition of crude or purified potato protease inhibitors to the test solution.

It is probably not wise to use fecal supernatants again (for reasons of safety), but a mixture of the 3 purified enzymes in appropriate concentrations has the same effect. Azocasein is a substrate which is hydrolyzed by several hydrolytic enzymes, but also enzyme-specific substrates can be tested. STI is just one of the inhibitors from soybeans inhibiting trypsin and chymotrypsin, but not elastase.

What is claimed is:

1. A method of treating or preventing perineal, peri-anal or peristomal inflammation caused by proteolytic activity of feces in a subject comprising:

administering topically an inhibitor of proteolytic activity to the perineal, peri-anal or peristomal area of the subject;

wherein the inhibitor is derived from a potato.

2. The method according to claim 1 wherein a diaper administers the inhibitor of proteolytic activity.

3. The method according to claim 1, wherein said inhibitor inhibits a protease's proteolytic activity, and the protease is selected from the group consisting of pancreatic and granulocyte protease.

4. The method according to claim 3, wherein said inhibitor inhibits the proteolytic activity of papain, pronase or both said papain and said pronase.

5. A method for treating or preventing perineal, peri-anal or peristomal inflammation caused by proteolytic activity of feces comprising:

subjecting the perineal, peri-anal or peristomal area of a mammal to a topical treatment with at least one inhibitor derived from a potato;

wherein at least one inhibitor is capable of inhibiting proteolytic activity of a protease.

6. The method according to claim 5 wherein said mammal is a human being.

7. The method according to claim 5, wherein said at least one inhibitor comprises potato juice.

8. The method according to claim 1 wherein said inhibitor is administered as an ointment, cream, gel, spray, rinsing fluid or powder containing said inhibitor.

9. The method according to claim 1 wherein a wipe is used to topically administer the inhibitor of proteolytic activity to said subject.

10. The method according to claim 5, wherein said inhibitor inhibits a protease's proteolytic activity, and the protease is selected from the group consisting of pancreatic and granulocyte proteases.

11. The method according to claim 10, wherein said inhibitor inhibits the proteolytic activity of papain, pronase or both papain and pronase.

* * * * *